United States Patent [19]
Koizumi

[11] Patent Number: 5,176,516
[45] Date of Patent: Jan. 5, 1993

[54] INSTRUMENT FOR MEASURING A REMAINING ALVEOLAR BONE

[76] Inventor: Masayuki Koizumi, 29-18 Higashiyamada 4-chome, Kouhoku-ku Yokohama-shi, Japan

[21] Appl. No.: 761,066

[22] Filed: Sep. 18, 1991

[30] Foreign Application Priority Data

Sep. 26, 1990 [JP] Japan ................... 2-100771

[51] Int. Cl.⁵ .................... A61C 19/04; G10B 1/00
[52] U.S. Cl. ................................. 433/72; 33/513; 33/514
[58] Field of Search ............... 433/72; 33/513, 514, 33/783, 784, 810, 811

[56] References Cited

U.S. PATENT DOCUMENTS

| | | | |
|---|---|---|---|
| 1,340,354 | 5/1920 | Williams | 33/513 |
| 2,540,555 | 2/1951 | Slaughter, Jr. | 433/72 |
| 4,229,883 | 10/1980 | Kobashi | 33/143 L |
| 4,277,237 | 7/1981 | Dermer | 433/72 |
| 4,536,964 | 8/1985 | Lazes | 33/199 R |
| 4,570,349 | 2/1986 | Finkelman et al. | 33/143 |

Primary Examiner—Gene Mancene
Assistant Examiner—Cindy A. Cherichetti
Attorney, Agent, or Firm—Cushman, Darby & Cushman

[57] ABSTRACT

A device for measuring the remaining portion of an alveolar bone is presented. The device comprises two elongated straight portions having each a leg portion. The elongate portions are connected to each other in slidable fashion similar to a caliper. The leg portions have width measuring probes which extend towards each other perpendicular to the leg portions. The widths measuring probes are arranged to penetrate the gum and contact opposite sides of the alveolar bone where by the the distance between the ends of the probes can be measured. The device also has a level measuring probe which extends from one of the elongate portions between the leg portions down towards the width measuring probes. The length measuring probe also penetrates the gum and measures how far down from the top of the alveolar bone, the width measuring probes are measuring.

17 Claims, 4 Drawing Sheets

INSTRUMENT FOR MEASURING A REMAINING ALVEOLAR BONE

BACKGROUND OF THE INVENTION

1. Field of the Invention

The present invention relates to an instrument for measuring a remaining alveolar bone, and particularly for measuring the width of a remaining alveolar bone at a predetermined level measured from the top of the remaining alveolar bone.

2. Description of Prior Art

Dental treatment is often necessary when a tooth is decayed or broken. One treatment of a decayed or deficient tooth is to embed an artificial tooth base on the remaining alveolar bone. Such an artificial tooth base is formed by coating a piece of titanium with apatite, and shaping it in the form of a cylinder, ranging from 3.3 mm to 4.0 mm across and 7 mm to 20 mm high.

As a matter of course an artificial tooth base must be smaller than the remaining alveolar bone in diameter, and it is desired to have the largest possible contact area. Therefore it is important to measure the remaining alveolar bone prior to treatment.

Usually an X-ray photograph is taken from the outside of the mouth of the remaining alveolar bone and the lateral length and height of the remaining alveolar bone are measured from the X-ray. Then, the width of the remaining alveolar bone is measured with the aid of a CT scanner, a costly and time consuming procedure.

Therefore a simpler method has been developed. A caliper consisting of a pair of legs connected together with a pivot and adjustable at any distance is used to measure the width of a remaining alveolar bone by pushing one leg of the caliper against one side of the remaining alveolar bone and the other leg to the other side. The width of the remaining alveolar bone can be determined in terms of the angle formed between the legs. However, this device does not indicate at which level of the remaining alveolar bone its width is determined. Therefore, the diameter and height of an artificial tooth base to be embedded cannot be determined.

SUMMARY OF THE INVENTION

One object of the present invention is to provide an instrument for determining the width of a remaining alveolar bone at a predetermined level which is measured down from the top of the remaining alveolar bone.

The present invention comprises a caliper formed of two pieces. One piece is an elongated scale having a lateral leg portion at one end. The other piece is a slider, having a lateral leg portion parallel to the leg portion of the elongated scale which slides longitudinally along the elongated scale of the other piece. The lateral leg of each piece has a width measuring probe fixed to its inside surface. The elongated scale piece has a level determining probe fixed to the elongated scale so that said level determining probe may extend in a direction perpendicular to said width measuring probe. Therefore, the width of said remaining alveolar bone may be determined at a predetermined level measured down from the top of said remaining alveolar bone by placing the width measuring probes of the parallel lateral legs of said two pieces in contact with the opposite sides of said remaining alveolar bone with said level determining probe on the top of said remaining alveolar bone.

In use, the level determining probe is pushed against the top of a remaining alveolar bone, and one or both pieces are made to slide until the width measuring probes of the parallel lateral legs of the pieces come into contact with opposite sides of the remaining alveolar bone. Then, the width of the remaining alveolar bone can be determined at a predetermined level measured down from the top of the remaining alveolar bone. Accordingly the diameter and height of an artificial tooth base appropriate for the remaining alveolar bone can be determined.

According to another aspect of the present invention the other piece may have a battery-operated liquid crystal display and associated memory to give a digital display of the measured width of the remaining alveolar bone. This feature is convenient for measuring in a limited space such as in the mouth.

According to still another aspect of the present invention, the width measuring probe may be detachably fixed to the inside surface of lateral leg of each piece. This is preferable from the sanitary point of view because new probes may be used for a different patient.

According to still another aspect of the present invention, a plurality of level determining probes of different lengths may be selectively inserted in holes made in the elongated scale. This permits selection of appropriate probes to fit a particular remaining alveolar bone, thereby improving the measuring accuracy.

According to still another aspect of the present invention, the level determining probe has lengthwise threads and the hole in the elongated scale is tapped, thereby permitting rotating adjustment of the length of the level determining Other objects and advantages of the present invention may be understood from the following description of the preferred embodiments of the present invention which are shown in the accompanying drawings.

DESCRIPTION OF PREFERRED EMBODIMENTS

Figure 1:
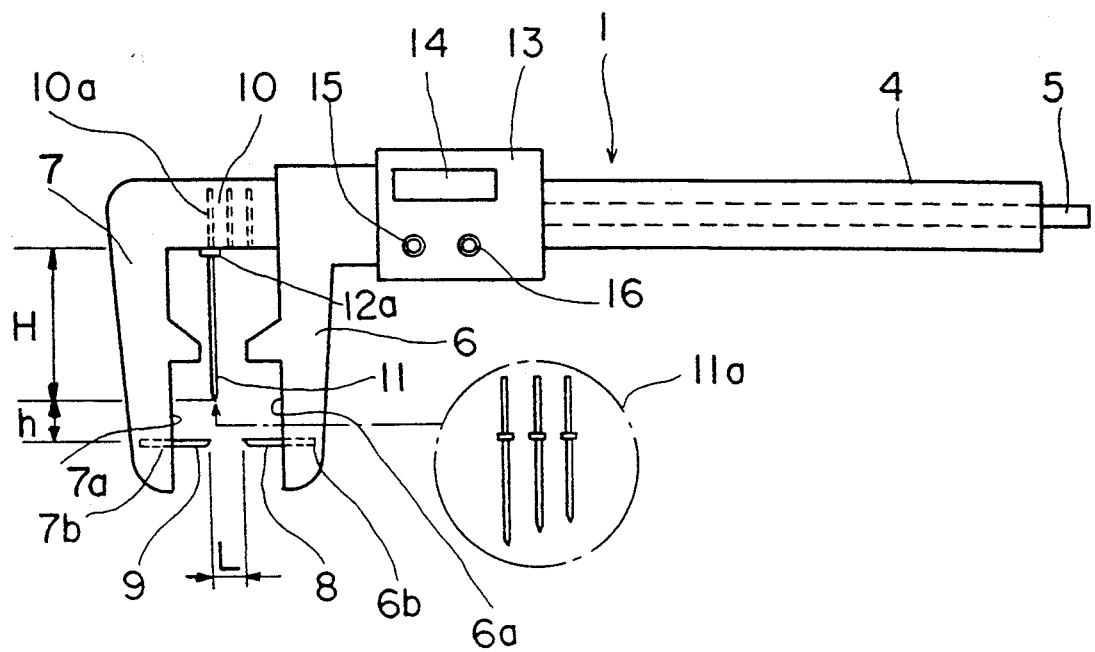
FIGURE 1 is a schematic view of an instrument for measuring the width of a remaining alveolar bone according to one embodiment of the present invention.

FIG. 1 shows an instrument for measuring the width of a remaining alveolar bone according to a first embodiment of the present invention. It comprises a caliper formed of two elongated straight pieces 4 and 5 sliding longitudinally across one another. Each piece has a lateral leg to be pushed against a remaining alveolar bone to be measured. The lateral legs 6 and 7 of each piece 4 and 5 have width measuring probes 8 and 9 detachably inserted in holes 6b and 7b made on inside surfaces 6a and 7a of lateral legs. Elongated straight piece 5 has a level determining probe 11 detachably inserted in of holes 10a made in elongated straight piece 5 so that level determining probe 11 may extend perpendicularly to width measuring probes 8 and 9. A plurality of level determining probes 11a of different lengths may be prepared, and selectively used. Piece 4 has a battery-operated liquid crystal display 13, on-and-off switch 15 and associated memory to give a digital display of the measured width of the remaining alveolar bone 2.

The manner in which instrument 1 is used to determine the width of a remaining alveolar bone 2 at a predetermined level is described First, an X-ray picture is taken to measure the height of the remaining alveolar bone 2 and the lateral length of the remaining alveolar bone 2 along gum 3.

Figure 2:
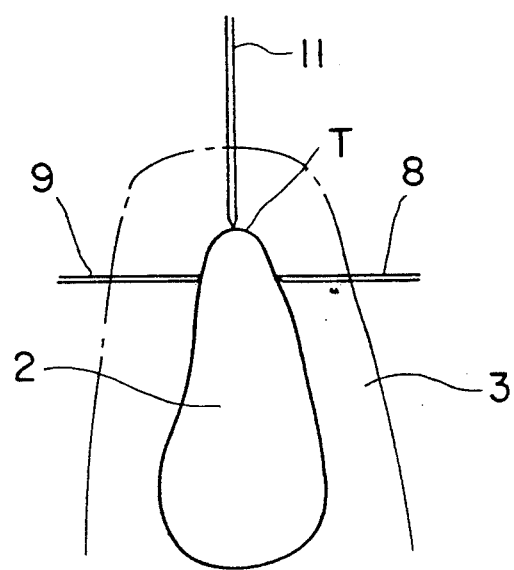
FIG. 2 shows the manner in which the width of a remaining alveolar bone can be determined at a predetermined level with the instrument of FIG. 1.
Figure 3:
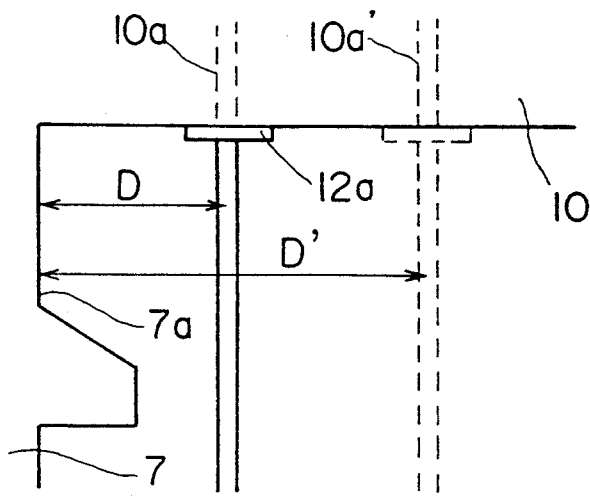
FIG. 3 is an enlarged schematic view of part of the instrument at which level determining probes may be attached.

Then, instrument 1 is used to measure the width of the remaining alveolar bone 2. Width measuring probes 8 and 9 are inserted in holes 6b and 7b made on inside surface 6a and 7a of legs 6 and 7. With information from the X-ray picture showing the height and lateral length of the remaining alveolar bone 2, level determining probe 11 of appropriate length is selected, and is inserted in one of holes 10a made in piece 5. As shown in FIG. 3, lateral distance D' is determined from the lateral length of the remaining alveolar bone 2 as appropriate for positioning level determining probe 11. Thus, hole 10a' is selected. As seen from FIG. 2, width measuring probe 9 is pushed against one side of remaining alveolar bone 2, and level determining probe 11 is pushed against the top of the remaining alveolar bone 2. Then, piece 4 is made to slide with respect to piece 5 until width measuring probe 9 is pushed against the other side of the remaining alveolar bone 2. Thus, the width of remaining alveolar bone 2 can be measured at the level (h) measured down from the top (T) of remaining alveolar bone 2.

Then, on-and-off switch 15 is turned on, and memory switch 16 is turned on, thus storing the measured width L of remaining alveolar bone 2. After taking instrument 1 out of the mouth the measured width can be read.

Measuring probes 8 and 9 may be changed for a different patient.

Figure 6:
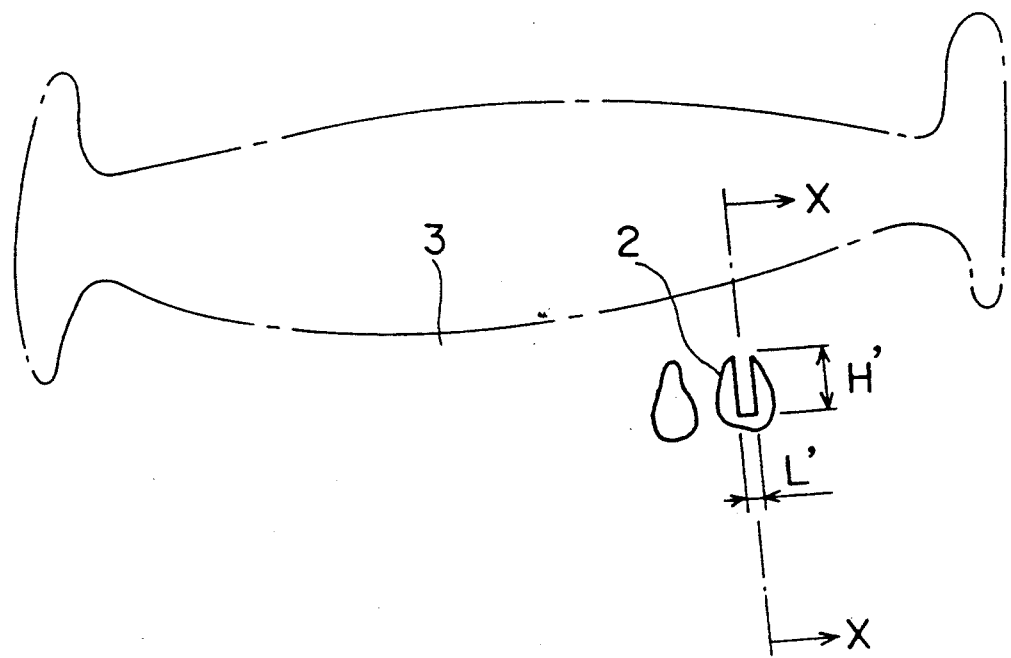
FIG. 6 is a schematic view of a remaining alveolar bone.
Figure 7:
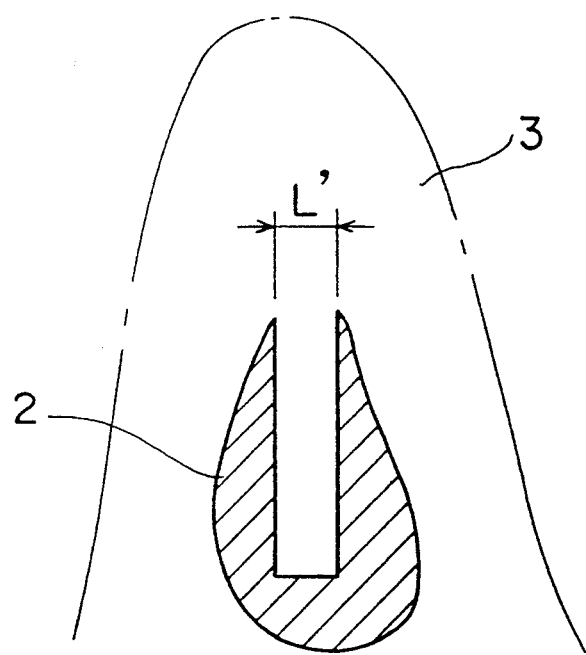
FIG. 7 is a sectional view of the remaining alveolar bone taken along the line X—X in FIG. 6.

From the so measured height, lateral length and width of remaining alveolar bone 2a, a correct cylindrical hole which is (H)' high and (L)' across can be made as shown in FIGS. 6 and 7, and an artificial tooth base can be embedded in place.

As may be understood from the above, instrument 1 permits measurement of the width of remaining alveolar bone 2 at a predetermined level, and therefore the length and diameter of an artificial tooth base and a hole to be made in remaining alveolar bone 2 can be accurately determined.

Figure 4:
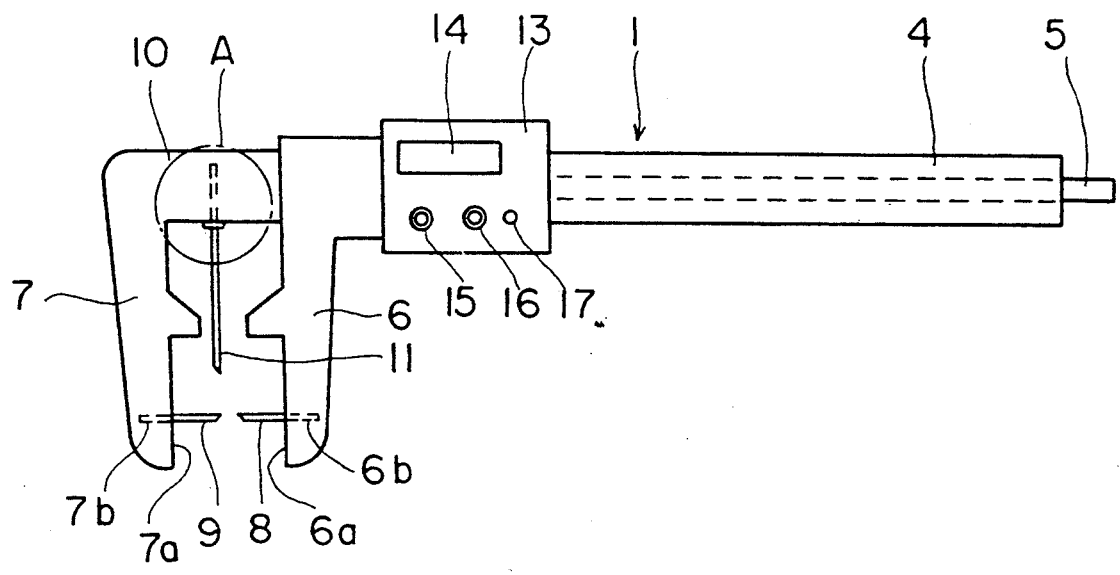
FIG. 4 is a schematic view of an instrument for measuring the width of a remaining alveolar bone according to another embodiment of the present invention.
Figure 5:
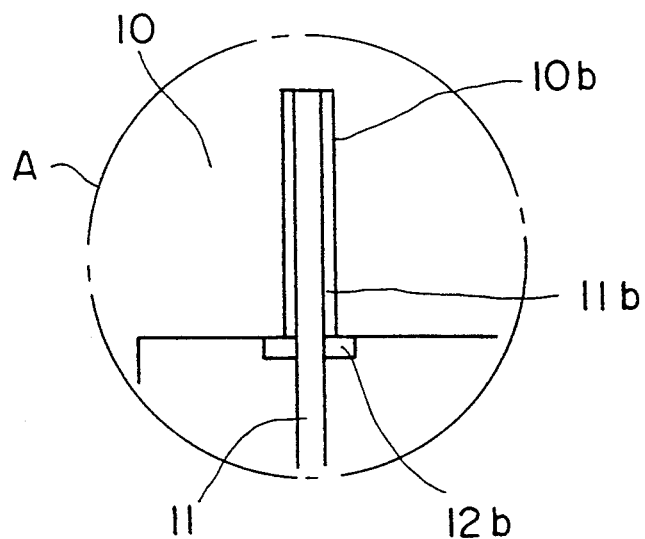
FIG. 5 is an enlarged view of the part which is circled and indicated by "A" in FIG. 4.

FIG. 4 shows schematically an instrument according to a second embodiment of the present invention. It is different from the instrument of the first embodiment only in that level determining probe 11 is threaded into hole 10b and can be adjusted in length by turning the probe. Specifically as seen from FIG. 5, level determining probe 11 is threaded to give male threads whereas hole 10b is tapped to give female threads, and ring 12b is integrally connected to level determining probe 11. Rotation of ring 12b adjusts the height of level determining probe 11, and hence the level measured down from the top T of remaining alveolar bone 2.

When level indication switch 17 is pushed, liquid display 14 indicates the longitudinal length of level determining probe 11. Digital display 13 may be separated from instrument 1, and a display data may be put on a disk. Then, data may be sent over transmission lines.

What is claimed is:

1. An instrument for measuring the width of a remaining alveolar bone comprising:
   a first elongated straight piece having a first leg portion extending perpendicularly from one end of the first elongated straight piece;
   a second elongated straight piece having a second leg portion extending perpendicularly from one end of the second elongated straight piece; said first and second elongated straight pieces being arranged for relative slidable movement along a longitudinal axis; and said first and second leg portions being parallel and perpendicular to said longitudinal axis; said first and second leg portions having opposing mating edges;
   a first width measuring probe extending from said first leg portion towards said second leg portion;
   a second width measuring probe extending from said second leg portion towards said first leg portion; said first and second width measuring probes for inserting through gum to reach edges of alveolar bone;
   a means for measuring the relative position of said width measuring probes; and
   wherein a plurality of level determining probes of different lengths are selectively inserted in one of a plurality of holes in one of said elongated straight pieces.

2. An instrument for measuring the width of a remaining alveolar bone according to claim 1 wherein said level determining probe has a threaded length and said holes in one of said elongated straight pieces are tapped, thereby permitting adjustment of said level determining probe length by rotation ofs aid level determining probe.

3. An instrument for measuring the width of a remaining alveolar bone comprising:
   a first elongated straight piece having a first leg portion extending perpendicularly from one end of the first elongated straight piece;
   a second elongated straight piece having a second leg portion extending perpendicularly from one end of the second elongated straight piece; said first and second elongated straight pieces being arranged for relative slidable movement along a longitudinal axis; and said first and second leg portions being parallel and perpendicular to said longitudinal axis; said first and second leg portions having opposing mating edges;
   a first width measuring probe extending from said first leg portion towards said second leg portion;
   a second width measuring probe extending from said second leg portion towards said first leg portion; said first and second width measuring probe for inserting through gum to reach edges of alveolar bone;
   a means for measuring the relative position of said width measuring probes;
   a level determining probe extending perpendicularly from one of said first and second elongated straight pieces at a position between said first and second leg portions, said level determining probe for inserting through gum to contact a top of a residual alveolar bone; and a means for measuring a distance between an end of said level measuring probe and a line between said width measuring probes.

4. An instrumetn for measuring the width of a remaining alveolar bone according to claim 3 wherein one of said elongated straight pieces has a battery-operated liquid crystal display and associated memory to give a digital display of measured width of said remaining alveolar bone.

5. An instrument for measuring the width of a remaining alveolar bone according to claim 3 wherein said first and second width measuring probes are detachably fixed to said opposing mating edges of said first and second leg portions, respectively.

6. An instrument for measuring the width of a remaining alveolar bone according to claim 3 wherein a plurality of level determining probes of different lengths are selectively inserted in one of a plurality of holes in one of said elongated straight pieces.

7. An instrument for measuring the width of a remaining alveolar bone according to claim 3 wherein said level determining probe has a threaded length and one of said elongated straight pieces has tapped holes for receiving said level determining probe, thereby permitting adjustment of said level determining probe length by rotation of said level determining probe.

8. An instrument for measuring the width of a remaining alveolar bone comprising:
   a first elongated straight piece having a first leg portion extending perpendicularly from one end of the first elongated straight piece;
   a second elongated straight piece having a second leg portion extending perpendicularly from one end of the second elongated straight piece; said first and second elongated straight pieces being arranged for relative slidable movement along a longitudinal axis; and said first and second leg portions being parallel and perpendicular to said longitudinal axis; said first and second leg portions having opposing mating edges;
   a first width measuring probe extending from said first leg portion towards said second leg portion;
   a second width measuring probe extending from said second leg portion towards said first leg portion;
   said first and second width measuring probes for inserting through gum to reach edges of alveolar bone;
   a means for measuring the relative position of said width measuring probes;
   a plurality of level determining probes each having a different length to be selectively engaged in a receptacle formed in oen of said first and second elongated straight pieces at intermediate positions between said first and second legs, said level determining probes for inserting through gum to contact a top of an alveolar bone; and
   a means for measuring a distance between an end of a level determining probe and a line between said width measuring probes.

9. An instrument for measuring the width of a remaining alveolar bone according to claim 8 wherein one of said elongated straight pieces has a battery-operated liquid crystal display and associated memory to give a digital display of measured widht of said remaining alveolar bone.

10. An instrument for measuring the width of a remaining alveolar bone according to claim 8 wherein said first and second width measuring probes are detachably fixed to said opposing mating edges of said first and second leg portions, respectively.

11. An instrument for measuring the width of a remaining alveolar bone according to claim 8 wherein a plurality of level determining probes of different lengths are selectively inserted in one of a plurality of holes in one of said elongated straight pieces.

12. An instrument for measuring the width of a remaining alveolar bone according to claim 8 wherein said level determining probes have lengths which are threaded and one of said elongated straight pieces has tapped holes for receiving said level determining probes, thereby permitting adjustment of said level determining probe length by rotation of said level determining probe.

13. An instrument for measuring dimensions of an object hidden by a covering article comprising:
   a first elongated straight piece having a first leg portion extending perpendicularly from one end of the first elongated straight piece;
   a second elongated straight piece having a second leg portion extending perpendicularly from one end of the second elongated straight piece; said first and second elongated straight pieces being arranged for relative slidable movement along a longitudinal axis; and said first and second leg portions being parallel and perpendicular to said longitudinal axis; said first and second leg portions having opposing mating edges;
   a first width measuring probe extending from said first leg portion towards said second leg portion;
   a second width measuring probe extending from said second leg portion towards said first leg portion;
   a second width measuring probe extending from said second leg portion towards said first leg portion;
   said first and second width measuring probes for inserting through said covering article to reach opposite edges of said object;
   a level determining probe extending from one of said first and second elongated straight pieces at a position between said first and second leg portions, said level determining probe for inserting through said covering article to contact with a top of said object; and
   a means for measuring a distance between an end of said level measuring probe and a line between said width measuring probes.

14. An instrument for measuring the width of a remaining hidden object according to claim 13 wherein one of said elongated straight pieces has a battery-operated liquid crystal display and associated memory to give a digital display of measured width of said remaining hidden object.

15. An instrument for measuring the width of a remaining hidden object according to claim 13 wherein said first and second width measuring probes are detachably fixed to said opposing mating edges of said first and second leg portions, respectively.

16. An instrument for measuring the width of a remaining hidden object according to claim 13 wherein a plurality of level determining probes of different lengths are selectively inserted in one of a plurality of holes in one of said elongated straight pieces.

17. An instrument for measuring the width of a remaining hidden object according to claim 13 wherein said level determining probe has a threaded length and one of said elongated straight pieces has tapped holes for receiving said level determining probel, thereby permitting adjustment of said level determinign probe length by rotation of said level determining probe.

* * * * *